US010935560B2

(12) United States Patent
Bottenus et al.

(10) Patent No.: US 10,935,560 B2
(45) Date of Patent: Mar. 2, 2021

(54) METHOD AND KIT FOR IDENTIFYING LUPUS ANTICOAGULANT (LA) ASSOCIATED WITH ANTIPHOSPHOLIPID SYNDROME

(71) Applicant: Instrumentation Laboratory Company, Bedford, MA (US)

(72) Inventors: Ralph E. Bottenus, Hillsborough, NJ (US); Zhenghua Cao, Nanuet, NY (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

(21) Appl. No.: 15/491,152

(22) Filed: Apr. 19, 2017

(65) Prior Publication Data

US 2017/0307641 A1    Oct. 26, 2017

Related U.S. Application Data

(60) Provisional application No. 62/327,028, filed on Apr. 25, 2016.

(51) Int. Cl.
| | | |
|---|---|---|
| *G01N 33/86* | (2006.01) | |
| *C12Q 1/56* | (2006.01) | |
| *G01N 33/564* | (2006.01) | |

(52) U.S. Cl.
CPC .............. *G01N 33/86* (2013.01); *C12Q 1/56* (2013.01); *G01N 33/564* (2013.01); *G01N 2800/24* (2013.01)

(58) Field of Classification Search
CPC .. G01N 33/86; G01N 33/564; G01N 2800/24; C12Q 1/56
USPC .......................................................... 435/13
See application file for complete search history.

(56) References Cited

U.S. PATENT DOCUMENTS

| | | | | |
|---|---|---|---|---|
| 7,932,021 | B2 * | 4/2011 | Greenfield ........... | G01N 33/564 435/2 |
| 2011/0129862 | A1 | 6/2011 | Nakamura et al. | |
| 2011/0240043 | A1 * | 10/2011 | Redington ........... | A61K 31/401 128/898 |
| 2012/0252743 | A1 * | 10/2012 | Herold ..................... | A61P 7/02 514/21.91 |
| 2014/0127726 | A1 | 5/2014 | Ieko et al. | |

FOREIGN PATENT DOCUMENTS

| | | |
|---|---|---|
| JP | 2002-517739 A | 6/2002 |
| JP | 2013-205087 A | 10/2013 |
| WO | 9964622 A1 | 12/1999 |

OTHER PUBLICATIONS

International Search Report and Written Opinion of corresponding PCT Application No. PCT/US2017/028286, filed Apr. 19, 2017, (16 pages).
Katrien Devreese, et al.; "Laboratory diagnosis of the antiphospholipid syndrome: a plethora of obstacles to overcome;" European Journal of Haematology 83; Jul. 2009; (pp. 1-16).
Roslyn Bonar, et al.; "The effect of the direct factor Xa inhibitors apixaban and rivaroxaban on haemostasis tests: a comprehensive assessment using in vitro and ex vivo samples;" Pathology, 48(1) (Jan. 2016); (pp. 60-71).
Helen Mani, et al.; "Ex vivo effects of low-dose rivaroxaban on specific coagulation assays and coagulation factor activities in patients under real life conditions;" Department of Internal Medicine, Division of Vascular Medicine, Johann Wolfgang Goethe-University Hospital Frankfurt/Main, Germany; Thrombosis and Haemostasis 109(1); Nov. 2012; (pp. 127-136).
D.R.J. Arachchillage, et al.; "Interactions between rivaroxaban and antiphospholipid antibodies in thrombotic antiphospholipid syndrome;" Journal of Thrombosis and Haemostasis; vol. 13(7); May 2015; (pp. 1264-1273).
J Arnout; "Antiphospholipid Syndrome: Diagnostic Aspects of Lupus Anticoagulants;" Center for Molecular and Vascular Biology; University of Leuven, Belgium; Thromb Haemost, vol. 86(1); 2001; (pp. 83-91).
M.E. Martinuzzo, et al.; "Frequent False-positive results of lupus anticoagulant tests in plasmas of patients receiving the new oral anticoagulants and enoxaparin;" International Journal of Laboratory Hematology; vol. 36(2); Sep. 2013; (pp. 144-150).
Katrien M.J. Devreese; "Evaluation of a new silica clotting time in the diagnosis of lupus anticoagulants;" Coagulation Laboratory, Department of Clinical Chemistry, Microbiology and Immunology, Ghent University Hospital De Pintelaan; Thrombosis Research; vol. 120(3); Jun. 2007; (pp. 427-438).
K.M.J. Devreese, et al.; "Mixing studies in lupus anticoagulant testing are required at least in some type of samples;" Journal of Thrombosis and Haemostasis; vol. 13(8); Jun. 2015; (pp. 1475-1478).
Genzen et al.; "Presence of Direct Thrombin Inhibitors Can Affect the Results and Interpretation of Lupus Anticoagulant Testing;" American Society for Clinical Pathology; 2005; pp. 586-593.
Triplett et al.; "Laboratory Diagnosis of Lupus Inhibitors: A Comparison of the Tissue Thromboplastic Inhibition Procedure with a New Platelet Neutralization Procedure;" American Society of Clinical Pathologists; 1982; pp. 678-682.
International Preliminary Report on Patentability for PCT Application No. PCT/US2017/028286, dated Oct. 30, 2018, (10 pages).
Japanese Office Action issued in corresponding Japanese application No. 2018-553480, dated Sep. 30, 2019, and English translation thereof, 12 pages.

(Continued)

*Primary Examiner* — Jennifer M. H. Tichy
(74) *Attorney, Agent, or Firm* — Burns & Levinson, LLP; Janine M. Susan (57) ABSTRACT

The invention described herein relates to a method and kit for the diagnosis of antiphospholipid syndrome in patients, wherein a coagulation inhibitor and normal pooled plasma mixture reduce the factor deficiency effect of patient plasma, and coagulation inhibitor interference in patient plasma, and increases specificity and the sensitivity for detecting lupus anticoagulants in the patient's blood in a phospholipid-dependent clotting assay.

13 Claims, 9 Drawing Sheets

(56) References Cited

OTHER PUBLICATIONS

Canadian Examination Report issued in corresponding Canadian application No. 3,020,980, dated Dec. 17, 2019, 6 pages.
Australian Examination Report issued in corresponding Australian application No. 2017257267, dated Dec. 18, 2019, 4 pages.

* cited by examiner

METHOD AND KIT FOR IDENTIFYING LUPUS ANTICOAGULANT (LA) ASSOCIATED WITH ANTIPHOSPHOLIPID SYNDROME

RELATED APPLICATIONS

This application claims priority to and benefit of U.S. provisional application No. 62/327,028 filed on Apr. 25, 2016, the entire content of which is incorporated by reference herein for all purposes.

TECHNICAL FIELD

The present invention is related to the field of clinical diagnostics, diagnosis of blood clotting disorders in particular, more specifically methods and kits for the diagnosis of the clotting disorder known as antiphospholipid syndrome (APS) in human patients by identifying lupus anticoagulants (LA) in patient blood by methods and kits that reduce clotting factor deficiency effects and reduce clotting inhibitor interference that are typically problematic in current methods for detecting LA, and kits thereof.

BACKGROUND

Antiphospholipid syndrome (APS) is a clinical disorder of hemostasis typically manifested as venous thrombosis, arterial thrombosis, recurrent fetal loss, premature birth, or miscarriage. Synonyms for APS include lupus anticoagulant syndrome because of its occasional association with the disorder, systemic lupus erythematosus. APS is currently the preferred term for antiphospholipid syndrome and will be used below.

Typical laboratory findings associated with APS include persistent elevation of so-called antiphospholipid antibodies also known as lupus anticoagulants, i.e., antibodies against membrane anionic phospholipids, e.g., anti-cardiolipin antibody or their associated plasma proteins, e.g., beta-2-glycoprotein; or abnormalities in phospholipid-dependent coagulation assays known as LA assays.

The mechanism of APS that alters normal homeostasis of coagulation and is manifested in a patient clinically as a hypercoagulable state is unclear. Mechanistic theories for the cause of hyper-coagulation include binding of a circulating protein to cell membrane phospholipids that are exposed by cell damage. For example, circulating beta-2-glycoprotein binds to exposed cell membrane phospholipids to form a protein-phospholipid complex. Some theories suggest that the protein-phospholipid complex may expose ligands on the complex that serve as targets for specific auto-antibodies.

Other suggested mechanisms underlying APS include enhanced production of auto-antibodies, production of antibodies against coagulation factors, enhanced platelet activity, and activation of endothelial cells for platelet binding. All of these proposed mechanisms underlie hyper-coagulation and pathological thrombosis in the patient.

APS diagnosis requires the interpretation of numerous laboratory tests that must be repeated over time to confirm the diagnosis. Lupus anticoagulants are identified by analyzing phospholipid-dependent clotting time assays known as lupus anticoagulant (LA) assays. An abnormal LA finding is believed to be the most reliable test for APS. Lupus anticoagulants are directed against plasma coagulation factors. The presence of lupus anticoagulants is manifested by a paradoxical prolongation of clotting time. Because clotting factor inhibitors and clotting factor deficiencies also prolong clotting time, the presence of these inhibitors and deficiencies in a patient's plasma sample complicates the diagnosis of APS. Clotting factor inhibitors include, for example, several broad categories such as specific antibodies against coagulation factors VIII and V, non-specific inhibitors such as heparin, as well as specific inhibitors such as thrombin inhibitors and direct factor Xa inhibitors.

The effect caused by the presence of factor deficiencies or factor inhibitors must be excluded for LA detection. To assist in assessing the role of factor inhibitors or deficiencies, a mixing study is conducted whereby platelet poor normal plasma having a normal complement of clotting factors, is mixed with the patient sample and the clotting test repeated to rule out a deficiency of abnormal clotting factors as the underlying cause of delayed coagulation. If the clotting time is normalized after the addition of normal plasma to the patient's plasma, the patient has a clotting factor deficiency. Mixing studies in which the patient plasma sample is diluted with normal (pooled) plasma is problematic for the diagnosis of APS because lupus anticoagulants in the patient sample are diluted. Thus, a patient plasma sample weakly positive for LA may be sufficiently diluted to render detection of low LA not possible. Therefore, patients weakly LA positive are overlooked in a mixing study. The low sensitivity of mixing studies for identification of lupus anticoagulants is one of the problems addressed by the invention described below.

Typical tests for detecting a coagulation disorder in which clotting time is measured include phospholipid-dependent assays, e.g., activated partial thromboplastin time (APTT), such as the APTT-based silica clotting time (SCT), dilute Russell's viper venom time (dRVVT), dilute prothrombin time (dPT), APTT-based kaolin clotting time (KCT). APTT-based platelet neutralization procedure (PNP), APTT-based hexagonal phase phospholipid neutralization test. As mentioned briefly above, currently the presence of LA is confirmed by a prolonged phospholipid-dependent clotting test result, the failure of mixing studies to correct the prolonged clotting time (mixing normal plasma into the test plasma to replace clotting factors), a normalization of the clotting time in the presence of high levels of phospholipid, and the absence of inhibitors of coagulation factors that would account for the prolonged clotting time.

APTT Screen and dRVVT Screen, two of several LA screening assays as mentioned above, are phospholipid-dependent clotting assays that use very low phospholipid concentrations in the assay of a patient's plasma. Accordingly, these tests are very sensitive to antiphospholipid antibodies. The sensitivity to antiphospholipid antibodies is confirmed by repeating the assay (termed a confirm assay) whereby high phospholipids concentrations are added to an identical phospholipid-dependent assay as was used to screen, to overwhelm the effects of the antiphospholipid antibody. A decrease in the level of clotting inhibition identified by a decrease in clotting time back into a normal range supports the presence of LA in the test plasma sample.

The results of the LA screening assays are expressed by Screen Ratio (Rs), an assay done in the presence of low levels of phospholipid, Confirm Ratio (Rc), an assay done in the presence of elevated levels of phospholipid, Screen-to-Confirm Ratio (R) and Normalized Screen-to-Confirm Ratio (NR) defined as follows:

$$R_s: \frac{\text{Screen Clotting Time (Test Sample)}}{\text{Screen Clotting Time } (NPP)}$$

-continued $$R_c: \frac{\text{Confirm Clotting Time (Test Sample)}}{\text{Confirm Clotting Time } (NPP)}$$

$$R: \frac{\text{Screen Clotting Time (Test Sample)}}{\text{Confirm Clotting Time (Test Sample)}}$$

$$NR: R_s/R_c$$

SUMMARY OF THE INVENTION

The present invention relates to the field of clinical diagnostics, diagnosis of blood clotting disorders in particular, more specifically methods and kits for the diagnosis of antiphospholipid syndrome (APS) in human patients by identifying lupus anticoagulants (LA) in patient blood by methods and kits that reduce clotting factor deficiency effects and reduce clotting inhibitor interference that occurs in present methods and kits for detecting LA. The embodiments of the invention disclosed herein have at least the following features in common: a coagulation inhibitor, low concentration phospholipid reagent, high phospholipid concentration reagent, and a phospholipid-dependent clotting time assay.

In one aspect, the invention is related to a method for detecting lupus anticoagulants (LA) associated with antiphospholipid syndrome (APS) in human patients. The method comprises a number of steps, for example, but not limited to the following steps. In step (a) the clotting time of plasma from a patient at risk for APS is detected by a phospholipid-dependent clotting assay that is measured in the presence of at least one coagulation inhibitor and a low concentration of phospholipid. In various embodiments of the method of the invention, the low concentration of phospholipid comprises a range of about 0.002 (g/l) to about 0.2 (g/l), preferred 0.002 (g/l) to 0.15 (g/l), more preferred 0.010 (g/l) to 0.10 (g/l) and most preferred 0.04 (g/l) to 0.08 (g/l).

In step (b), the clotting time of plasma from the patient at risk for APS is detected by the phospholipid-dependent clotting assay of step (a) that is measured in the presence of the coagulation inhibitor of step (a) and a concentration of phospholipid higher than the low concentration of phospholipid in step (a). In various embodiments of the method of the invention, the high concentration of phospholipid comprises a range of about preferred 0.2 (g/l) to 5.0 (g/l), more preferred 0.5 (g/l) to 3.0 (g/l) and most preferred 1.0 (g/l) to 2.0 (g/l).

A ratio of the clotting time detected in the patient plasma in step a) to the clotting time detected in the patient plasma in step b) is determined. The patient ratio is compared to reference interval and cutoff values established with preferably at least 40 normal, healthy subjects. The mean of the reference interval is used for normalizing LA assays, and the patient sample ratio is compared to the cutoff value. The cutoff value is established as suggested in current LA guidelines as either the value above the 99$^{th}$ percentile of the distribution of normal samples or as the mean +2SD interval of the parametric distribution of normal samples. If the ratio is greater than the cutoff, the patient is likely to have LA associated with APS and repeat testing is suggested after 12 weeks to confirm persistent presence of circulating antiphospholipid antibodies. In various embodiments of the method of the invention, the exemplary cutoff ratio is expressed as a ratio of NR between 1.00 and 1.20, preferably between 1.00 and 1.15, more preferably between 1.00 and 1.10.

The effect on clotting that may be caused by a clotting factor deficiency or the presence of clotting inhibitors such as pharmaceuticals, taken by patients with cardiac arrhythmias or patients at risk of a cerebral infarct is determined by conducting a mixing assay. In a mixing assay, the patient's plasma is diluted with normal pooled plasma and the phospholipid-dependent clotting assay is repeated. The mixing study will identify whether a patient's clotting disorder is related to a deficiency in a clotting factor. In various embodiments of the method of the invention, dilutions of the patient's plasma sample may be, for example, 1:1, 1:2, 1:3 or 1:4 with normal pooled plasma.

The addition of a coagulation inhibitor and normal pooled plasma to the patient plasma in a phospholipid-dependent clotting assay reduces interference caused by the presence of a factor deficiency or a coagulation inhibitor in the plasma and increases specificity and the sensitivity of the method for detecting lupus anticoagulants.

The phospholipid-dependent clotting assay used in the method of the invention may be selected from the group consisting of activated partial thromboplastin time (APTT), dilute Russell's viper venom time (dRVVT), APTT-based platelet neutralization procedure (PNP), APTT-based hexagonal phase phospholipid neutralization test, APTT-based kaolin clotting time (KCT), APTT-based silica clotting time (SCT) and dilute prothrombin time (dPT) to name a few such phospholipid-dependent clotting assays.

In a particular embodiment of the method of invention, the coagulation inhibitor is a combination of coagulation inhibitors, for example, more than one thrombin inhibitor, more than one Xa inhibitor, or one or more thrombin inhibitors and one or more factor Xa inhibitors.

In one embodiment of the method according to the invention, the at least one coagulation inhibitor is a thrombin inhibitor.

Thrombin inhibitors may be selected from the group consisting of d-phenylalanyl-1-prolyl-1-arginine-chloromethyl ketone (PPACK), I-2581, hirudin, hirudin derivatives, lepirudin, desirudin, hirudin analogues, bivalirudin, argatroban, melagatran, dabigatran, and their combinations.

In another embodiment of the method of the invention, the at least one coagulation inhibitor is a factor Xa inhibitor.

Factor Xa inhibitors may be selected from the group consisting of rivaroxaban, apixaban, edoxaban, betrixaban, antistasin, Tick Anticoagulant Protein (TAP), and combinations thereof.

In another aspect, the invention is directed to a kit for detecting lupus anticoagulants associated with antiphospholipid syndrome in a patient plasma sample. In one embodiment of the invention, the kit comprises at least one coagulation inhibitor and normal pooled plasma. Alternatively, the kit comprises a phospholipid-dependent clotting reagent comprising a low concentration of phospholipid, at least one coagulation inhibitor, and, a phospholipid-dependent clotting reagent comprising a concentration of phospholipid that is higher than the low concentration of phospholipid. In various embodiments of the kit, the low concentration of phospholipid comprises a range of about 0.002 (g/l) to about 0.2 (g/l). In various embodiments of the kit, the high concentration of phospholipid comprises a range of about 0.2 (g/l) to about 5.0 (g/l).

In various embodiments of the kit according to the invention, the phospholipid-dependent clotting reagent comprises at least one of APTT, dRVVT, APTT-based platelet neutralization procedure (PNP), APTT-based hexagonal phase phospholipid neutralization test, APTT-based kaolin clotting time (KCT), APTT-based silica clotting time (SCT) and dilute prothrombin time (dPT).

In one embodiment of the kit according to the invention, the coagulation inhibitor of the kit according to the invention, comprises at least one thrombin inhibitor.

The thrombin inhibitor may be selected from the group consisting of d-phenylalanyl-1-prolyl-1-arginine-chloromethyl ketone (PPACK), I-2581, hirudin, hirudin derivatives (e.g., lepirudin and desirudin), hirudin analogues (e.g., bivalirudin), argatroban, melagatran, dabigatran, and their combinations.

In an alternative embodiment, of the kit according to the invention the at least one coagulation inhibitor comprises at least one factor Xa inhibitor. The factor Xa inhibitor may be selected from the group consisting of rivaroxaban, apixaban, edoxaban, betrixaban, antistasin, Tick Anticoagulant Protein (TAP) and their combinations.

As discussed above with respect to the method of the invention and applied to the kit described herein, the effect on clotting that may be caused by a clotting factor deficiency or the presence of clotting inhibitors such as pharmaceuticals taken by patients with cardiac arrhythmias or by patients who are at risk for a cerebral infarct is determined by conducting a mixing assay. In a mixing assay provided in the contents of the kit, the patient's plasma is mixed with normal pooled plasma and then the phospholipid-dependent assay is repeated. The mixing assay will identify a deficiency in clotting factors in the patient's plasma. In various embodiments of the kit according to the invention, normal pooled plasma may be included in the kit with sufficient volume for dilutions of the patient's plasma sample by 1:1, 1:2, 1:3 or 1:4 with normal pooled plasma.

Various combinations and arrangements of reagents and containers in the kit are contemplated by the invention. For example, a coagulation inhibitor and a phospholipid-dependent clotting reagent comprising a first low concentration of phospholipid are packaged in a container as part of the kit. Alternatively, a coagulation inhibitor and a second phospholipid-dependent clotting reagent comprising a high concentration of phospholipid may be packaged in a container, the normal pooled plasma may be packaged in the same container as a coagulation inhibitor, or alternatively, all reagents may be packaged in individual containers in the kit. Containers mean but are not limited to a vial, envelope, or tube, for holding a powdered form or a liquid form of reagent.

These and other objects, along with advantages and features of the present invention herein disclosed, will become apparent through references to the following description, and the claims. Furthermore, it is to be understood that the features of the various embodiments described herein are not mutually exclusive and can exist in various combinations and permutations.

As used herein, "tested patient plasma" and "normal pooled plasma" (NPP) are platelet poor plasmas.

As used herein, the term "comparing" encompasses comparing the clotting time or a ratio of clotting times determined on a plasma sample with a suitable cutoff ratio specified elsewhere herein. The "comparing" step of the method of the present invention may be carried out manually or by a computing device such as an automated clinical analyzer, e.g., the ACL TOP® Family (Instrumentation Laboratory Company, Bedford, Mass.). The value of the plasma ratio and the cutoff ratio is compared one to the other and the comparison may be automatically carried out by a computer program executing an algorithm for the comparison. The computer program will provide the desired assessment in suitable output format. For a computer assisted comparison, the value of the determined amount may be compared to values corresponding to suitable cutoff values which are stored in a database by a computer program. The computer program may further evaluate the result of the comparison, i.e., automatically provide the desired assessment in a suitable output format.

As used herein, the term "ratio of clotting times" encompasses a ratio of clotting times normalized to a suitable reference value for normal, healthy subjects. The suitable reference value shall mean the average clotting time for a reference interval established with a cohort of normal, healthy subjects, the clotting time for a sample derived from a cohort of normal, healthy subjects, or a ratio calculated from such clotting times. A suitable reference value may be determined from a reference plasma sample to be analyzed together i.e. simultaneously, subsequently or at least close in time with the test (patient) plasma sample.

As used herein, cutoff ratio shall mean an upper limit ratio, for example, which allows for allocation of a sample into a group of plasma samples having lupus anticoagulants, or into a group of plasma samples not having lupus anticoagulants. Such a cutoff ratio can be a threshold or a cut-off which separates the two groups. Cutoff ratios can be calculated for plasmas from a cohort of normal patients not identified as having APS based on the average or mean values for the assays described herein by applying standard statistical methods as recommended in current LA guidelines.

As used herein, the term "kit" refers to a collection of components, preferably provided in separate or within a single container. The components include but are not limited to reagents including chemicals, plasma, or buffers, which may be provided separately in vials, for example, within the container. Alternatively two or more components may be combined together in, for example, a vial within the container. The container also includes instructions for conducting the LA assay using at least some of the components within the container with or without components from another source, e.g., a different kit. The kit may also comprise standards which reflect the reference amounts as described and referred to elsewhere herein.

As used herein, an APTT reagent means phospholipid-dependent activated partial thromboplastin time reagent in which the clotting time is measured, for example, HemosIL® Silica Clotting Time (Instrumentation Laboratory Company).

As used herein, dRVVT reagent means a phospholipid-dependent dilute Russell's viper venom time reagent in which the clotting time is measured, for example, HemosIL® dRVVT Screen and Confirm tests (Instrumentation Laboratory Company).

As used herein, the terms "assay" and "test" are used interchangeably.

BRIEF DESCRIPTION OF THE FIGURES

FIG. 4A illustrates that PPACK at increasing concentrations showed different effects on the dRVVT Screen test of normal plasma samples and LA positive plasma samples. FIG. 4B illustrates that PPACK at increasing concentrations did not show different effects on the dRVVT Confirm test.

FIG. 6 illustrates in graph form the effect of PPACK concentrations on the NR of dRVVT test. The LA positive sample at 3 concentrations (undiluted, 1:1 or 1:3 diluted with NPP), had an NR of 1.76, 1.42 and 1.19, respectively at 1000 ng/ml PPACK in the automated mixing study (1:1 dilution with NPP/PPACK material). Even the most dilute sample (an effective eight fold dilution of the original sample with NPP) still remains as a positive LA result.

FIG. 7A illustrates that I-2581 had similar impact on the Screen-to-Confirm Ratio of LA positive and NPP samples in the absence of PPACK with both slightly decreased at the presence of I-2581. At the presence of 350 nM PPACK, the effect from I-2581 on the Screen-to-Confirm Ratio remained similar for LA positive and NPP samples.

FIG. 7B illustrates that I-2581 contributed to a slight decrease in the normalized ratio with or without the combined use of PPACK.

FIG. 8A illustrates that hirudin increased the Screen-to-Confirm Ratio for both NPP (from 1.02 in the absence of hirudin to 1.18 at 1000 ng/ml hirudin) and LA positive sample (from 1.41 in the absence of hirudin to 2.14 at 1000 ng/ml hirudin), although the effect on NPP sample was rather small. FIG. 8B illustrates that when argatroban was used as the inhibitor, the Screen-to-Confirm Ratio responded in a different pattern: the ratio for LA positive sample (squares) didn't change, while the ratio for NPP (crosses) decreased noticeably (from 1.06 in the absence of argatroban to 0.9 at 500 ng/ml argatroban). Hirudin and argatroban displayed a synergistic effect when used together (triangles for NPP and diamonds for LA positive sample). A synergistic effect may occur with the combination of other coagulation inhibitors, e.g., PPACK and rivaroxaban.

FIG. 9A illustrates the normalized ratio increased from 1.39 (without thrombin inhibitor use) to 1.81 (at 1000 ng/ml hirudin) for the LA positive sample. FIG. 9B illustrates that argatroban increased the Normalized Ratio from 1.34 to 1.57 (at 500 ng/ml argatroban, squares) by decreasing the NPP Screen-to-Confirm Ratio. When hirudin and argatroban were used together, the normalized ratio decreased from 1.72 (200 ng/ml hirudin alone) to 1.66 (200 ng/ml hirudin and 500 ng/ml argatroban) for the LA positive sample (diamonds).

DESCRIPTION OF THE INVENTION

Anticoagulants against thrombin and factor Xa prolong clotting times in LA assays by effectively reducing the available amounts of those factors in the reaction mixture. However, the effect from the anticoagulants on LA negative and LA positive plasma specimens differs. Coagulation inhibitors, e.g., thrombin and factor Xa inhibitors, in an LA assay increases sensitivity to LA antibodies, which allows reliable mixing studies to be performed to address the interference caused by factor deficiency or endogenous coagulation factors. The difference provides methods for improving the interpretation of LA assays both when the test plasma sample is diluted with normal plasma to normalize clotting factors and when it is not. Therefore, LA sensitivity, for example, detecting weak LA positive plasma, can be significantly increased using reagents with anticoagulant added without sacrificing the LA assay specificity. Further, the invention described herein boosts the LA signal in so-called "mixing assays", discussed above, for detecting LA.

The current invention employs a methodology whereby selected anticoagulants are added to LA assays to achieve improved assay sensitivity and specificity and to render a more reliable automated mixing study (adding normal plasma substantially free of platelets (NPP) to the patient plasma sample and repeating the clotting assay) to address factor deficiency and factor inhibitor problems in LA detection for the diagnosis of APS. Specifically, according to the invention described herein, the synergistic effects from different inhibitors including but not limited to thrombin inhibitors PPACK, hirudin, hirudin derivatives, e.g., lepirudin and desaridin, hirudin analogues, e.g., bivaluridin, argatroban, melagatran, dabigatran, I-2581, and their combinations, when added to standard phospholipid-dependent assays provide unique tools in optimizing the sensitivity and specificity in LA detection and diagnosis of APS. The amount of coagulation inhibitor added must be optimized to increase the clotting time ratio of LA positive samples while continuing the correction of the LA negative samples that have factor deficiencies or factor inhibitors that are corrected by the mixing study plasma added to the sample.

According to one aspect, the invention is a kit for aiding in the detection of lupus anticoagulants for the diagnosis of APS in a patient. In one embodiment of the invention, the kit includes at least one coagulation inhibitor, e.g., such as but not limited to a thrombin inhibitor, for example, but not limited to the thrombin inhibitors detailed above, and normal plasma, pooled or otherwise. In another embodiment, the kit above further includes, or is intended to be used with an LA assay such as an APTT reagent, for example, APTT-based silica clotting time (SCT), APTT-based platelet neutralization procedure (PNP), APTT-based hexagonal phase phospholipid neutralization test, APTT-based kaolin clotting time (KCT), having a low phospholipid concentration, in the range of 0.002 (g/l) to 0.2 (g/l), preferably 0.01 (g/l), and the LA assay having a high phospholipid concentration, in the range of 0.2 (g/l) to 5.0 (g/l), preferably 1.0 (g/l).

In another aspect, the invention is a method for detecting lupus anticoagulants to aid in the diagnosis of APS in a patient. In one embodiment of the method of the invention, a coagulation screen clotting assay is conducted by mixing a patient's plasma with one or more coagulation inhibitors, a thrombin inhibitor, for example, one or more of the thrombin inhibitors or factor Xa inhibitors above, and a phospholipid-dependent APTT reagent with low phospholipid concentration. The screen clotting time is measured. A coagulation confirm clotting assay is also done on the patient's plasma by mixing the patient's sample with the thrombin inhibitor used in the screen assay, and the phospholipid in the presence of a high concentration phospholipid APTT reagent, and the confirm clotting time is measured.

In an alternative embodiment, for example, high and low phospholipid APTT is replaced with high and low phospholipid as disclosed above in a dRVVT assay or dilute Prothrombin Time assay in the screen and confirm clotting assays of the patient's plasma.

In another embodiment of the method of the invention, for example, a factor Xa screen clotting assay is conducted by mixing a patient's plasma with a factor Xa inhibitor, for example, but not limited to, rivaroxaban, apixaban, edoxaban, betrixaban, antistasin, Tick Anticoagulant Protein (TAP) and combinations thereof and an APTT reagent with low phospholipid concentration as described above. The clotting time is measured. A confirm clotting assay is also done on the patient's plasma by mixing the patient's sample with the factor Xa inhibitor used in the factor Xa screen assay of the patient's plasma sample, and the high phospholipid concentration APTT reagent as described above APTT reagent. The confirmed clotting time is measured.

In an alternative embodiment, high and low phospholipid APTT is replaced with high and low phospholipid dRVVT in the screen and confirm clotting assays of the patient's plasma.

For each of the assays above, irrespective of the clotting inhibitor used in the assay, the measured screen assay clotting time of a patient sample is compared to the measured screen assay clotting time of normal platelet poor plasma and expressed as a ratio (Rs). Additionally, the measured confirm assay clotting time of a patient sample is compared to the measured confirm assay clotting time of normal platelet poor plasma and expressed as a ratio (Rc). A normalized ratio (NR) is expressed as Rs/Rc. The NR is compared to a cutoff ratio established from normal, healthy subjects.

In a preferred embodiment of the invention, the cutoff ratio is derived from preferably at least 40 normal, healthy subjects. The cutoff value is established as suggested in current LA guidelines as either the value above the $99^{th}$ percentile of the distribution of normal samples or as the mean +2SD interval of the parametric distribution of normal samples. A test plasma ratio being greater than the cutoff ratio is indicative of the presence of lupus anticoagulants in the test plasma and repeat testing is suggested after 12 weeks to confirm persistent presence of circulating antiphospholipid antibodies.

In a preferred embodiment of the invention, the exemplary cutoff ratio is expressed as a ratio of NR between about 1.00 and about 1.20, preferably between about 1.00 and about 1.15, more preferably between about 1.00 and about 1.10.

In a preferred embodiment of the invention, the clotting time of normal platelet poor plasma is established from at least 40 normal, healthy subjects. The average clotting time of the normal, healthy subjects is used to normalize the test plasma clotting time.

In an alternative embodiment, the clotting time of normal platelet poor plasma is established from a pool of normal, healthy subjects. The clotting time of the pooled normal, healthy subjects is used to normalize the test plasma clotting time.

Exemplary Studies

Figure 1A:
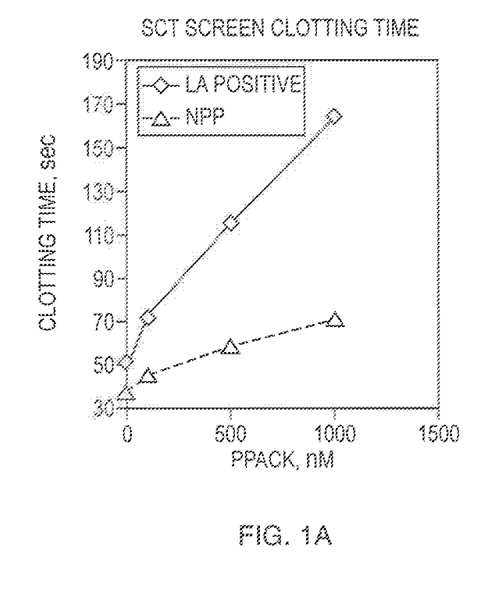
FIGS. 1A-B illustrate the effect of d-phenylalanyl-1-prolyl-1-arginine-chloromethyl ketone (PPACK) concentrations on the clotting time for A PTT-based silica clotting (SCT Screen) and APTT-based silica clotting time confirm (SCT Confirm) according to one embodiment of the invention. PPACK at increasing concentrations showed different effects on the SCT Screen Test of normal plasma samples and LA positive plasma samples but not on the SCT Confirm Test.
Figure 1B:
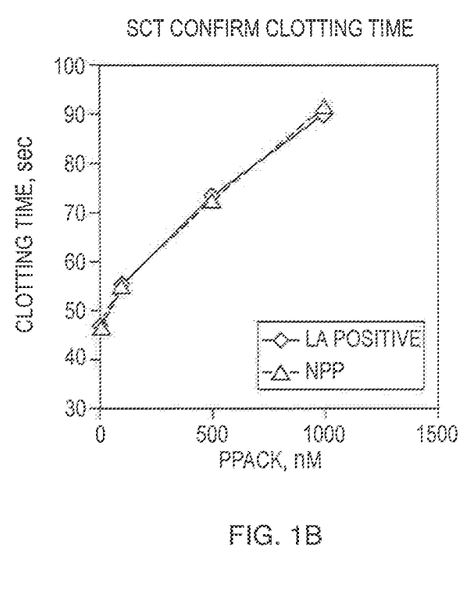
Figure 2:
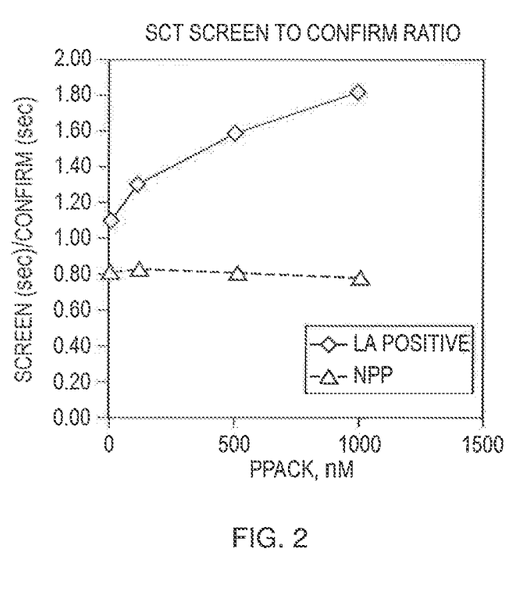
FIG. 2 illustrates in graph form the effect of PPACK concentrations on the Screen-to-Confirm Ratio of the SCT Assay according to one embodiment of the invention. Increasing PPACK concentrations increased the Screen-to-Confirm Ratio of LA positive sample from 1.09 to 1.82. The Screen-to-Confirm Ratio of normal pooled plasma (NPP) remained the same.
Figure 3:
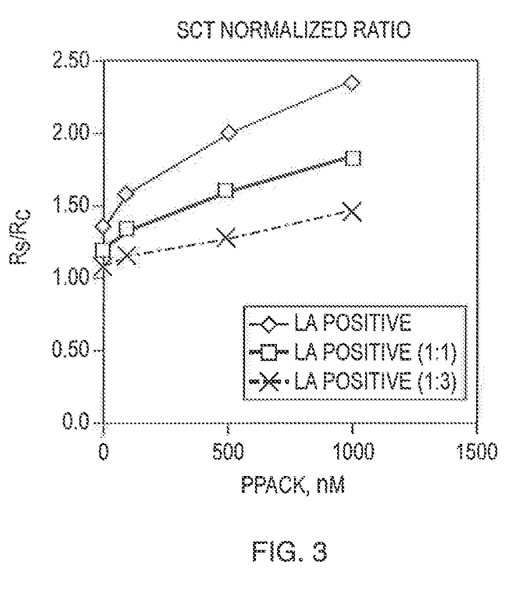
FIG. 3 illustrates in graph form the effect of PPACK concentration on the Normalized Ratio (NR) of S(CT Assay according to one embodiment of the invention. The LA positive sample at 3 concentrations (undiluted, 1:1 or 1:3 diluted with NPP), had a NR of 2.34, 1.82, and 1.46, respectively at 1000 ng/ml of PPACK in the automated mixing study (1:1 dilution with NPP/PPACK material). Even the most dilute sample (an effective eight fold dilution of the original sample with NPP) still remains as a positive LA result.

D-phenylalanyl-1-prolyl-1-arginine-chloromethyl ketone (PPACK) is a synthetic peptide that irreversibly binds to the catalytic site of thrombin. Referring to FIGS. 1-3, the use of PPACK in an SCT assay is shown where a plasma test sample was mixed with a LA negative plasma sample pool in a 1:1 ratio during testing (i.e., in a mixing study setting). By a mixing study, clotting factors that are present in normal plasma are added to the test plasma suspected of having a coagulation disorder. If the coagulation abnormality (prolongation of clotting time) is corrected, the test plasma is missing a clotting factor and does not have LA.

The introduction of PPACK in an LA assay causes the prolongation of the clotting time for both SCT Screen and SCT Confirm, however, the effect of PPACK on SCT Screen (low phospholipid concentration) and SCT Confirm (higher phospholipid concentration) assays differs significantly for LA positive and LA negative (platelet poor NPP) samples. Referring to FIGS. 1A-B, while the effect of PPACK on SCT Screen and SCT Confirm is similar for the LA negative sample, PPACK has much greater impact on SCT Screen than on SCT Confirm for the LA positive samples. Thus, referring to FIG. 2, for the LA negative sample, the screen-to-confirm ratio decreased slightly at high PPACK concentrations (R was 0.81, 0.83 and 0.78 at 0, 100 and 1000 nM PPACK, respectively), and for the LA positive sample, the screen-to-confirm ratio increased from 1.09 in the absence of PPACK to 1.82 at 1000 nM PPACK, resulting in normalized ratios in the range of 1.36 to 2.34 for the LA positive sample when normalized to the LA negative sample at the same PPACK concentration (see FIG. 3).

The effect of PPACK on LA detection is further analyzed on the LA positive sample diluted with LA negative sample in different ratios (1:1 and 1:3 of LA positive: LA Negative). When the LA positive sample was diluted 4-fold with LA negative sample, the LA was not detectable in the absence of PPACK (NR: 1.08) but became clearly LA positive in the presence of 1000 nM PPACK (NR: 1.46) thereby underscoring the increased sensitivity of the method disclosed herein.

Figure 4A:
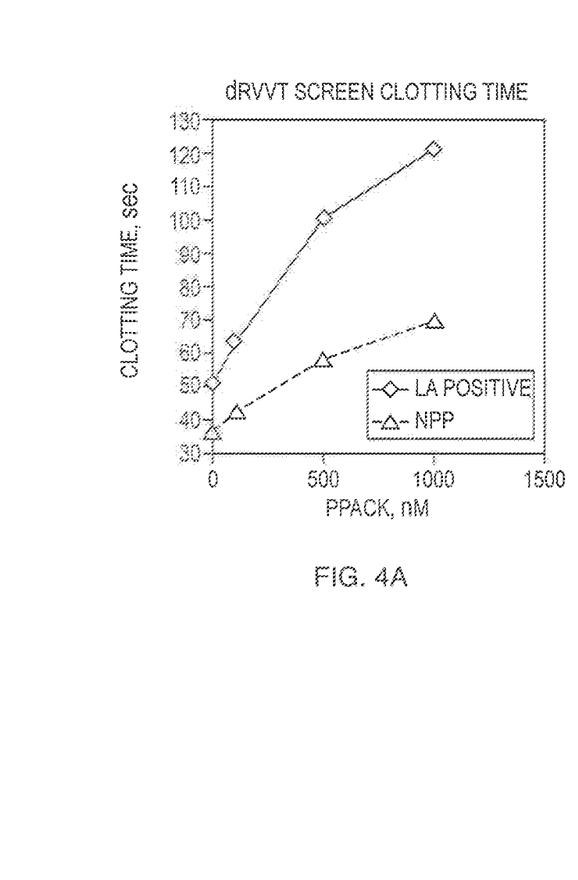
FIGS. 4A-4B illustrate in graph form the effect of PPACK concentration on the clotting time for dRVVT Screen test and dRVVT Confirm test according to one embodiment of the invention.
Figure 4B:
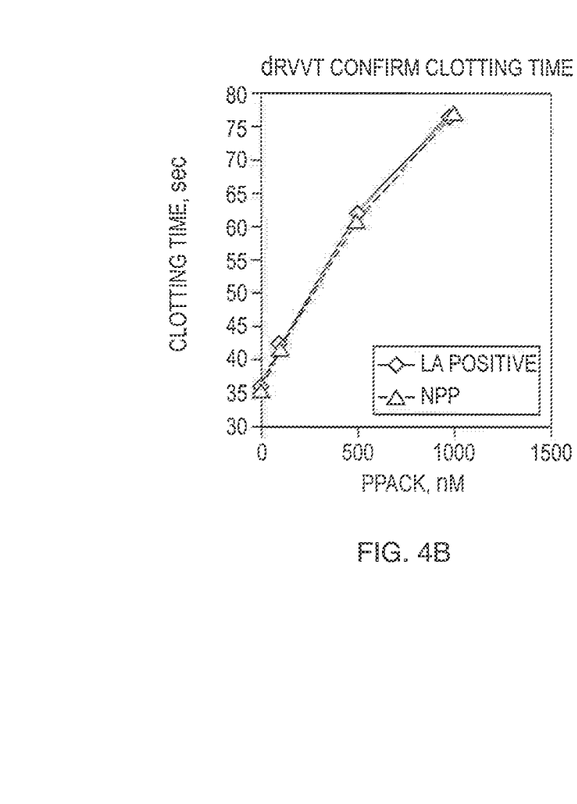
Figure 5:
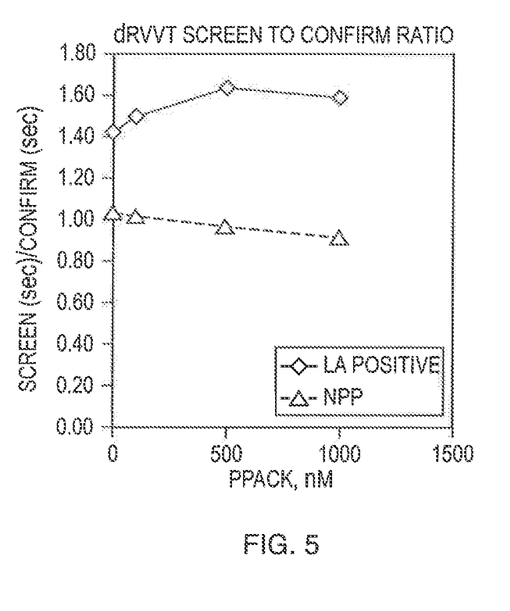
FIG. 5 illustrates in graph form the effect of PPACK concentration on the Screen-to-Confirm Ratio of dRVVT test. Increasing PPACK concentrations increased the Screen-to-Confirm Ratio of the LA positive sample from 1.42 to 1.58, while it decreased the Screen-to-Confirm ratio of NPP from 1.02 to 0.91.
Figure 6:
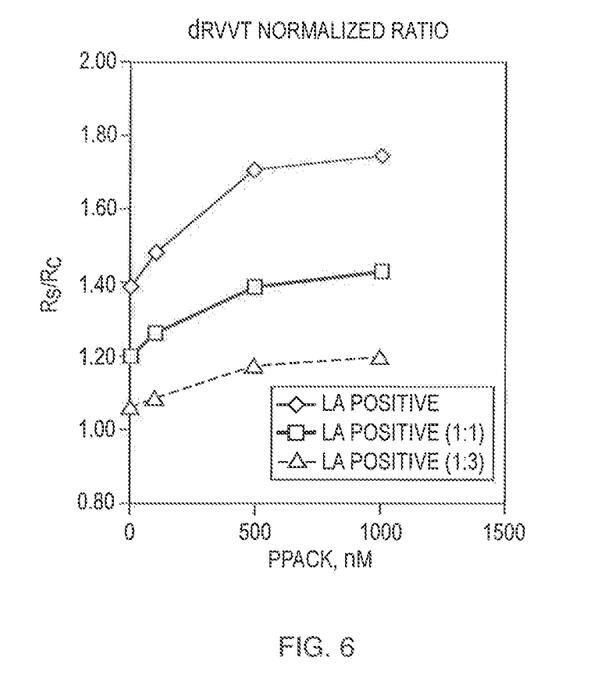

Referring now to FIGS. 4-6, the PPACK model demonstrates the same use of thrombin inhibitors on the dRVVT test, where test samples were mixed and diluted with LA negative sample in a 1:1 ratio during testing (i.e., in a mixing study setting).

The use of PPACK in the SCT assay and dRVVT assay demonstrates that much enhanced assay sensitivity may be achieved even when the sample is diluted in a mixing study, thus making the mixing study more useful in detecting LA when the complicating effects from factor deficiency and factor inhibitors are minimized by the addition of platelet poor normal plasma. The observed decrease in normalized ratio for LA negative samples also indicates that a slight improvement in assay specificity is likely.

When patient plasma samples (n=18) with various factor deficiencies (LA negative, factor V deficient, factor VIII deficient, factor VII deficient, factor VIII/von Willebrand factor deficient, factor IX deficient, factor X deficient, factor XI deficient, factor XII deficient, and LA positive plasma samples) were tested with HemosIL® dRVVT assay (Table 1) (no PPACK), two plasma samples with factor V deficiency and one sample with factor X deficiency showed high levels of screen ratio (Rs). Among these three abnormal plasma samples exhibiting a clotting factor deficiency, two samples failed the dRVVT Confirm test. Accordingly, for these two failed plasma samples, the normalized ratio (NR) could not be calculated.

TABLE 1

Patient Samples Assayed by HemosIL ® dRVVT Screen and dRVVT Confirm

| | | dRVVT | | | | | |
|---|---|---|---|---|---|---|---|
| Sample ID | Description | Screen, s | Confirm, s | S/C (R) | Screen (Rs) | Confirm (Rc) | S/C (NR) |
| 0114 LA NEG | LA Negative Pool | 36.4 | 35.3 | 1.03 | 1.00 | 1.00 | 1.00 |
| 0114 S01 | FVDef (con) | 155.9 | Failed | N/A | 4.28 | N/A | N/A |
| 0114 S02 | FVDef (con) | 57.5 | 59.9 | 0.96 | 1.58 | 1.70 | 0.93 |
| 0114 S03 | FVIIIDef (con) | 34.2 | 34.0 | 1.01 | 0.94 | 0.96 | 0.98 |
| 0114 S04 | FVIIIDef (con) | 34.7 | 33.2 | 1.05 | 0.95 | 0.94 | 1.01 |
| 0114 S05 | FVIII (con)/vWF Def | 34.0 | 33.7 | 1.01 | 0.93 | 0.95 | 0.98 |
| 0114 S06 | FVIII (con)/vWF Def | 33.8 | 33.4 | 1.01 | 0.93 | 0.95 | 0.98 |
| 0114 S07 | FIXDef (con) | 36.1 | 35.4 | 1.02 | 0.99 | 1.00 | 0.99 |
| 0114 S08 | FIXDef (con) | 34.4 | 33.0 | 1.04 | 0.95 | 0.93 | 1.01 |
| 0114 S09 | FXDef (con) | 216.0 | Failed | N/A | 5.93 | N/A | N/A |
| 0114 S10 | FXDef (con) | 52.9 | 49.6 | 1.07 | 1.45 | 1.41 | 1.03 |
| 0114 S11 | FXIDef (con) | 37.2 | 35.2 | 1.06 | 1.02 | 1.00 | 1.02 |
| 0114 S12 | FXIDef (con) | 32.7 | 33.5 | 0.98 | 0.90 | 0.95 | 0.95 |
| 0114 S13 | FXIIDef (con) | 31.5 | 31.1 | 1.01 | 0.87 | 0.88 | 0.98 |
| 0114 S14 | FXIIDef (acq) | 38.4 | 40.0 | 0.96 | 1.05 | 1.13 | 0.93 |
| 0114 S15 | LA Postive | 86.1 | 35.8 | 2.41 | 2.37 | 1.01 | 2.33 |
| 0114 S16 | LA Postive | 105.2 | 37.8 | 2.78 | 2.89 | 1.07 | 2.70 |
| 0114 S17 | LA Postive | 78.6 | 36.4 | 2.16 | 2.16 | 1.03 | 2.09 |

Table 2 results disclose that when the above plasma samples (LA negative, factor V deficient, factor VIII deficient, factor VII deficient, factor VIII/von Willebrand factor deficient, factor IX deficient, factor X deficient, factor XI deficient, factor XII deficient, and LA positive plasma samples) were tested with dRVVT in the presence of 35) nM PPACK in a mixing study setting (1:1 test plasma sample to NPP ratio), only one factor V deficiency sample showed slightly higher screen ratio (1.28 with PPACK vs 4.28 with HemosIL® dRVVT Screen). The study reported the normalized ratio correctly for all plasma samples and addressed issues with factor deficiency (Table 2).

As discussed below, while the PPACK model demonstrates a significant improvement in the current LA testing methodology, the uniqueness of various thrombin and factor Xa inhibitors provides an even richer inventory of arsenal in tackling the LA test sensitivity and specificity, with the use of different inhibitor combinations.

Figure 7A:
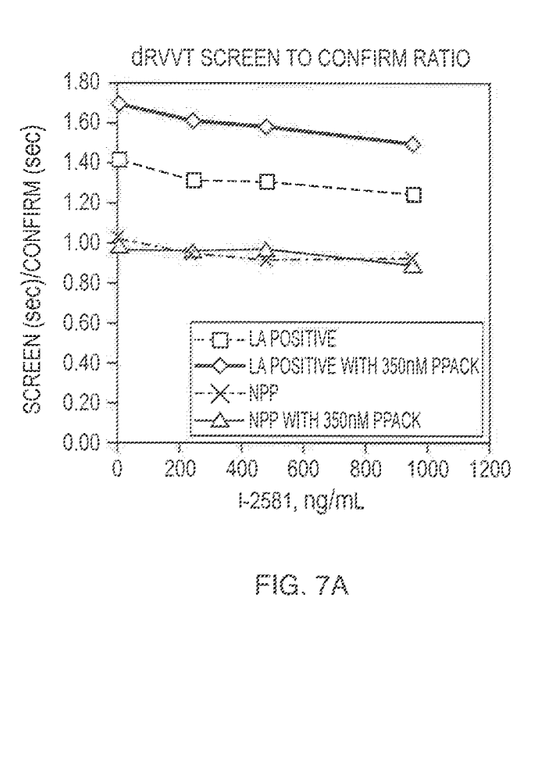
FIGS. 7A-B illustrate in graph form the effect of I-2581 and the combined use of I-2581 and PPACK on the Screen-to-Confirm Ratio and the NR of the dRVVT Assay according to one embodiment of the invention.
Figure 7B:
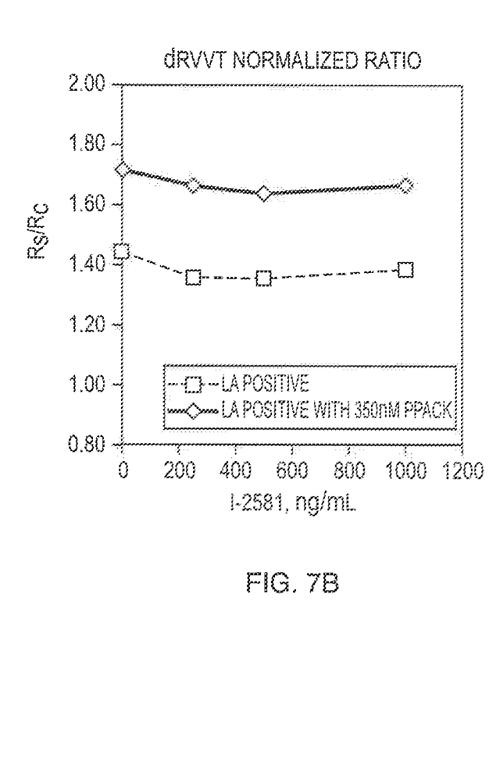

Referring to FIG. 7, I-2581, a synthetic thrombin inhibitor, decreases the dRVVT screen-to-confirm ratio for both LA positive and NPP samples when used in the dRVVT assay, which could potentially further increase the LA assay specificity when used together with an inhibitor with the capability of increasing the LA assay sensitivity.

TABLE 2

Patient Samples Assayed by HemosIL ® dRVVT Screen and dRVVT Confirm in the Presence of PPACK with a 1:1 Mixing Study Setting

| | | 0 nM PPACK | | | | | | 350 nM PPACK | | | | | |
|---|---|---|---|---|---|---|---|---|---|---|---|---|---|
| Sample ID | Description | Screen, s | Confirm, s | S/C (R) | Screen (Rs) | Confirm (Rc) | S/C (NR) | Screen, s | Confirm, s | S/C (R) | Screen (Rs) | Confirm (Rc) | S/C (NR) |
| 0114 LA NEG | LA Negative Pool | 35.8 | 34.6 | 1.03 | 1.0 | 1.0 | 1.0 | 49.6 | 50.4 | 0.98 | 1.00 | 1.00 | 1.00 |
| 0114 S01 | FVDef (con) | 43.4 | 39.1 | 1.11 | 1.21 | 1.13 | 1.07 | 63.3 | 62.8 | 1.01 | 1.28 | 1.25 | 1.02 |
| 0114 S02 | FVDef (con) | 33.7 | 36.1 | 0.93 | 0.94 | 1.04 | 0.90 | 46.9 | 54.2 | 0.87 | 0.95 | 1.08 | 0.88 |
| 0114 S03 | FVIIIDef (con) | 34.3 | 33.2 | 1.03 | 0.96 | 0.96 | 1.00 | 49.7 | 47.9 | 1.04 | 1.00 | 0.95 | 1.05 |
| 0114 S04 | FVIIIDef (con) | 34.4 | 32.5 | 1.06 | 0.96 | 0.94 | 1.02 | 49.3 | 48.5 | 1.02 | 0.99 | 0.96 | 1.03 |
| 0114 S05 | FVIII (con)/vWF Def | 34.4 | 33.7 | 1.02 | 0.96 | 0.97 | 0.99 | 48.4 | 49.2 | 0.98 | 0.98 | 0.98 | 1.00 |
| 0114 S06 | FVIII (con)/vWF Def | 34.4 | 33.4 | 1.03 | 0.96 | 0.97 | 1.00 | 48.6 | 48.9 | 0.99 | 0.98 | 0.97 | 1.01 |
| 0114 S07 | FIXDef (con) | 34.7 | 34.7 | 1.00 | 0.97 | 1.00 | 0.97 | 41.1 | 50.5 | 0.95 | 0.97 | 1.00 | 0.97 |
| 0114 S08 | FIXDef (con) | 34.6 | 32.8 | 1.05 | 0.97 | 0.95 | 1.02 | 48.5 | 48.9 | 0.99 | 0.98 | 0.97 | 1.01 |
| 0114 S09 | FXDef (con) | 41.8 | 39.7 | 1.05 | 1.17 | 1.15 | 1.02 | 60.7 | 59.2 | 1.03 | 1.22 | 1.17 | 1.04 |
| 0114 S10 | FXDef (con) | 36.4 | 36.2 | 1.01 | 1.02 | 1.05 | 0.97 | 51.1 | 51.4 | 0.99 | 1.03 | 1.02 | 1.01 |
| 0114 S11 | FXIDef (con) | 34.6 | 34.4 | 1.01 | 0.97 | 0.99 | 0.97 | 48.8 | 49.7 | 0.98 | 0.98 | 0.99 | 1.00 |
| 0114 S12 | FXIDef (con) | 33.3 | 33.8 | 0.99 | 0.93 | 0.98 | 0.95 | 46.8 | 47.7 | 0.98 | 0.94 | 0.95 | 1.00 |
| 0114 S13 | FXIIDef (con) | 32.4 | 31.7 | 1.02 | 0.91 | 0.92 | 0.99 | 44.9 | 45.3 | 0.99 | 0.91 | 0.90 | 1.01 |
| 0114 S14 | FXIIDef (acq) | 34.4 | 35.5 | 0.97 | 0.96 | 1.03 | 0.94 | 49.4 | 53.4 | 0.93 | 1.00 | 1.06 | 0.94 |
| 0114 S15 | LA Postive | 71.2 | 34.1 | 2.09 | 1.99 | 0.99 | 2.02 | 121.8 | 49.7 | 2.45 | 2.46 | 0.99 | 2.49 |
| 0114 S16 | LA Postive | 80.8 | 35.5 | 2.28 | 2.26 | 1.03 | 2.20 | 137.4 | 51.7 | 2.66 | 2.77 | 1.03 | 2.70 |
| 0114 S17 | LA Postive | 65.3 | 34.4 | 1.90 | 1.82 | 0.99 | 1.83 | 107.3 | 49.8 | 2.15 | 2.16 | 0.99 | 2.19 |

As shown in Table 2, the normalized ratio reported for LA positive samples in the presence of 350 nM PPACK was not lower than the corresponding results from HemosIL® dRVVT (see Table 1), which indicates that the methodology in a mixing study setting in the presence of 350 nM PPACK has better sensitivity than the HemosIL® dRVVT assay.

Figure 8A:
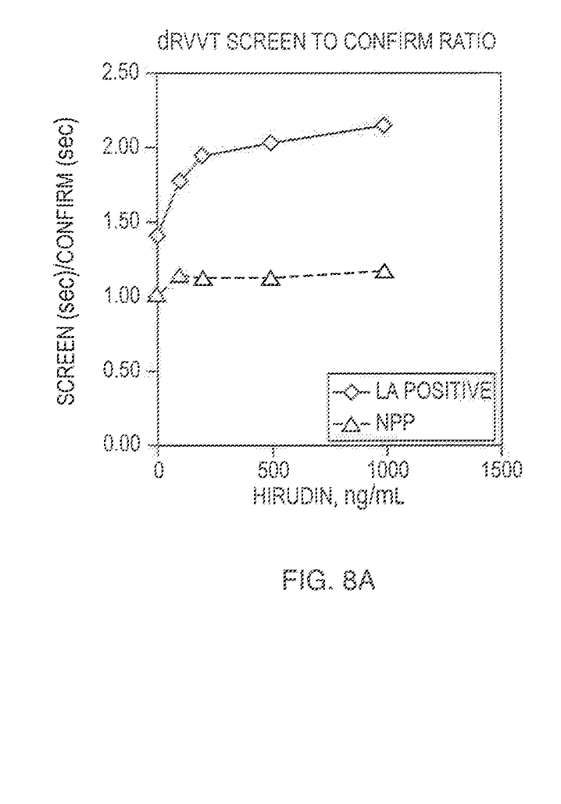
FIGS. 8A-B illustrate in graph form the effect of hirudin, argatroban and their combined use on the Screen-to-Confirm Ratio of the dRVVT Assay according to one embodiment of the invention.
Figure 8B:
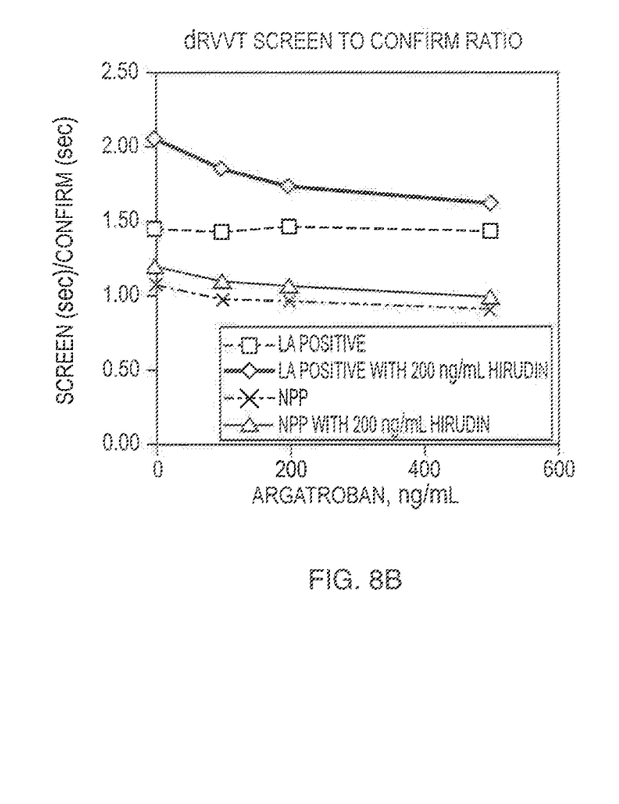
Figure 9A:
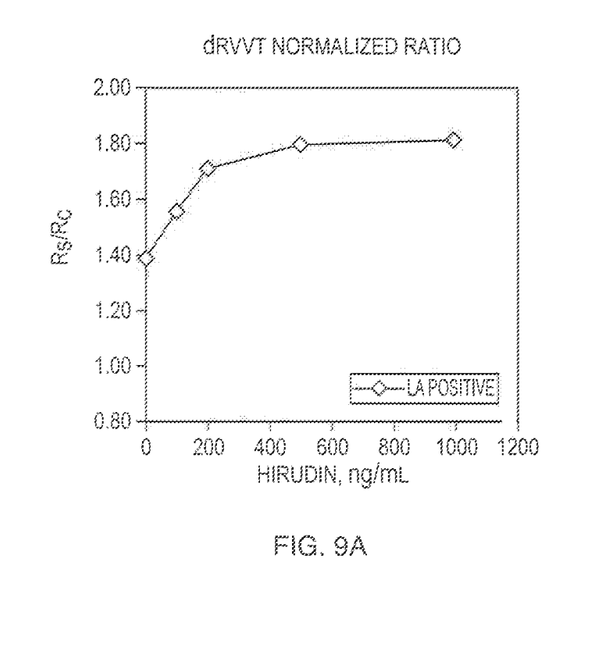
FIGS. 9A-B illustrate in graph form the effect of hirudin, argatroban and their combined use on the normalized ratio of the dRVVT Assay according to one embodiment of the invention.
Figure 9B:
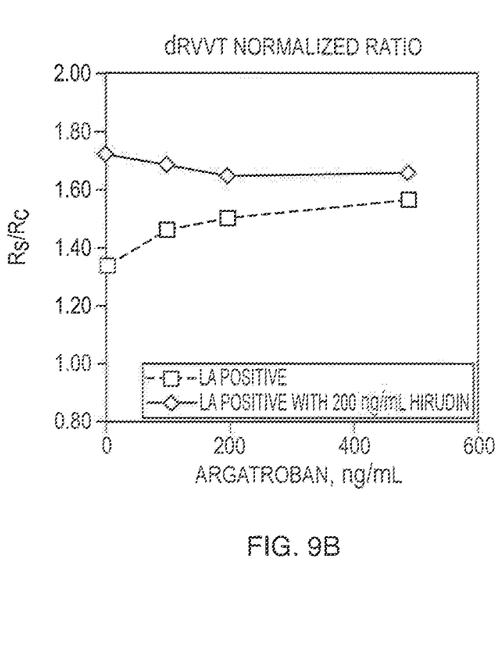

In yet another embodiment, referring to FIG. 8, the combined use of hirudin and argatroban, two direct thrombin inhibitors, provides another example of the power of such combinations in relation to the heterogeneity of LA antibody target antigens. Hirudin increased the dRVVT Screen-to-Confirm Ratio for both LA positive and NPP samples (left panel, FIG. 8). Although the use of hirudin in the dRVVT test increased the normalized ratio of the LA positive sample as shown in FIG. 9, it could also easily misclassify normal samples as weak positive without normalization (FIG. 8). The use of argatroban showed limited increase in NR for LA positive samples (FIG. 9) by decreasing the Screen-to-Confirm Ratio for NPP (FIG. 8). Hirudin and argatroban, when used together in the mixing study, increased the LA test sensitivity (NR: 1.66 at 200 ng/ml hirudin and 500 ng/ml argatroban as shown in FIG. 9), as compared to results for the HemosIL® dRVVT assay (NR: 1.64, data not shown), while the potential misclassification for normal samples is minimized (FIG. 8).

In another aspect, the invention is a system for aiding in the diagnosis of APS, comprising a clinical analyzer, e.g., but not limited to the ACL TOP® Family of clinical analyzers (Instrumentation Laboratory Company, Bedford, Mass.), configured to (a) bring a plasma sample in contact with a first phospholipid-dependent clotting assay reagent comprising a low concentration of phospholipid and a coagulation inhibitor for a sufficient amount of time to determine a first clotting time, (b) a second phospholipid-dependent clotting assay reagent comprising a high concentration of phospholipid and a coagulation inhibitor for a sufficient amount of time to determine a second clotting time, (c) a computing device having a processor in operable communication with said analyzer unit, and, (d) a non-transient machine readable media including instructions executable by the processor, the instructions when executed transform the first and second clotting times into a ratio, compare the ratio to a cutoff ratio, and establish an aid for diagnosing lupus anticoagulants based on the result of said comparison to said cutoff ratio.

Accordingly, the invention described here provides a new methodology in detecting LA. The usage of thrombin inhibitor PPACK on the detection of LA using the APTT and dRVVT assays is served as a model for the methodology in this invention. This invention leads to improved LA assay sensitivity/specificity and better utilization of mixing studies. Various thrombin inhibitors and factor Xa inhibitors, or a combination of such inhibitors, can be used to replace PPACK. Specifically, the current invention demonstrates that the synergistic effect from different coagulation inhibitors may be used to optimize the LA test sensitivity and specificity in relation to the heterogeneity of LA antibody target antigens.

We claim:

1. A method for detecting lupus anticoagulants associated with antiphospholipid syndrome in a patient, comprising:
    a) detecting a first clotting time of a plasma sample from said patient in a phospholipid-dependent clotting assay measured after the addition of more than one coagulation inhibitor comprising a combination of thrombin inhibitors or a combination of a thrombin inhibitor and a factor Xa inhibitor, and the addition of a first concentration of phospholipid to the patient sample;
    b) detecting a second clotting time of the plasma sample in the phospholipid clotting assay measured after the addition of the more than one coagulation inhibitors of step a), and the addition of a second concentration of phospholipid higher than said first concentration of phospholipid in step a) to the patient sample; and,
    c) determining a patient ratio between the first and the second clotting times of the patient plasma and comparing the patient ratio to a cutoff ratio normalized to a suitable reference value established from normal, healthy subjects, wherein the patient ratio determined in step c) being greater than the cutoff ratio is indicative of the presence of lupus anticoagulants in the test plasma.

2. The method of claim 1 wherein each of the phospholipid-dependent clotting assays of step a) and the phospholipid-dependent clotting assay of step b) further comprise platelet poor plasma.

3. The method of claim 1 wherein the phospholipid-dependent assay comprises activated partial thromboplastin time (APTT).

4. The method of claim 1 wherein the phospholipid-dependent assay is selected from the group consisting of dilute Russell's viper venom time (dRVVT), APTT-based platelet neutralization procedure (PNP), APTT-based hexagonal phase phospholipid neutralization test, APTT-based kaolin clotting time (KCT), APTT-based silica clotting time (SCT) and dilute prothrombin time (dPT).

5. The method of claim 1 wherein the combination of thrombin inhibitors are or the thrombin inhibitor in combination with a factor Xa inhibitor is selected from the group consisting of D-phenylalanyl-L-prolyl-L-arginine-chloromethyl ketone (PPACK), I-2581, hirudin, hirudin derivatives, lepirudin, desirudin, hirudin analogues, bivalirudin, argatroban, melagatran, dabigatran, and combinations thereof.

6. The method of claim 1 wherein the factor Xa inhibitor is selected from the group consisting of rivaroxaban, apixaban, edoxaban, betrixaban, antistasin, Tick Anticoagulant Protein (TAP), and combinations thereof.

7. The method of claim 2 further comprising diluting said patient plasma sample with normal pooled plasma.

8. The method of claim 2 further comprising diluting said patient plasma sample 1:1 with normal pooled plasma.

9. The method of claim 2 further comprising diluting said patient plasma sample 1:2, 1:3 or 1:4 with said normal pooled plasma.

10. The method of claim 1 wherein said first concentration of phospholipid comprises a range of about 0.002 g/l to about 0.2 g/l and said second concentration of phospholipid comprises a range of about 0.2 g/l to about 5.0 g/l.

11. The method of claim 1 wherein said cutoff ratio is a ratio of normalized screen-to-confirm ratio (NR) between about 1.00 and about 1.20.

12. The method of claim 1 wherein the combination of thrombin inhibitors is PPACK and I-2581.

13. The method of claim 1 wherein the combination of thrombin inhibitors is argatroban and hirudin.

* * * * *